United States Patent
Odom et al.

(10) Patent No.: US 7,731,717 B2
(45) Date of Patent: Jun. 8, 2010

(54) SYSTEM AND METHOD FOR CONTROLLING RF OUTPUT DURING TISSUE SEALING

(75) Inventors: Darren Odom, Longmont, CO (US); Craig Weinberg, Denver, CO (US); Amy Denham, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 716 days.

(21) Appl. No.: 11/500,688

(22) Filed: Aug. 8, 2006

(65) Prior Publication Data

US 2008/0039836 A1 Feb. 14, 2008

(51) Int. Cl.
 *A61B 18/18* (2006.01)
(52) U.S. Cl. .............................. 606/51; 606/41; 606/52
(58) Field of Classification Search ............. 606/32–34, 606/41, 50–51
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,279,753 A | 4/1942 | Knopp |
| 2,827,056 A | 3/1958 | Degelman |
| 2,849,611 A | 8/1958 | Adams |
| 3,058,470 A | 11/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |

(Continued)

FOREIGN PATENT DOCUMENTS

DE 179607 3/1905

(Continued)

OTHER PUBLICATIONS

International Search Report EP 06000708.5 dated Apr. 21, 2006.

(Continued)

*Primary Examiner*—Roy D Gibson

(57) ABSTRACT

An electrosurgical system for sealing tissue is disclosed which includes an electrosurgical forceps having a shaft member and a jaw member disposed at a distal end thereof. The jaw members are movable from a first position in spaced relation relative to one another to at least one subsequent position wherein the jaw members cooperate to grasp tissue therebetween. Each of the jaw members including a sealing plate which communicates electrosurgical energy through tissue held therebetween. The jaw members are adapted to connect to an electrosurgical generator. The system also includes one or more sensors which determine a gap distance between the sealing plates of the jaw members and a microprocessor which is adapted to communicate with the sensor and measure an initial gap distance between the sealing plates as well as to generate a desired gap distance trajectory based on the initial gap distance. The microprocessor is further adapted to communicate with the at least one sensor in real time to adjust output level of the electrosurgical generator as a function of the measured gap distance during the sealing process.

14 Claims, 6 Drawing Sheets

U.S. PATENT DOCUMENTS

| | | |
|---|---|---|
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,863,339 A | 2/1975 | Reaney et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,233,734 A | 11/1980 | Bies |
| 4,237,887 A | 12/1980 | Gosner |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| D263,020 S | 2/1982 | Rau, III |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,375,218 A | 3/1983 | DiGeronimo |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,418,692 A | 12/1983 | Guay |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,655,215 A | 4/1987 | Pike |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,754,892 A | 7/1988 | Retief |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,846,171 A | 7/1989 | Kauphusman et al. |
| 4,848,335 A | 7/1989 | Manes |
| 4,860,745 A | 8/1989 | Farin et al. |
| 4,862,889 A | 9/1989 | Feucht |

| | | | | | |
|---|---|---|---|---|---|
| 4,887,199 A | 12/1989 | Whittle | 5,400,267 A | 3/1995 | Denen et al. |
| 4,890,610 A | 1/1990 | Kirwan et al. | 5,403,311 A | 4/1995 | Abele et al. |
| 4,903,696 A | 2/1990 | Stasz et al. | 5,403,312 A | 4/1995 | Yates et al. |
| 4,907,589 A | 3/1990 | Cosman | 5,409,000 A | 4/1995 | Imran |
| 4,922,210 A | 5/1990 | Flachenecker et al. | 5,409,485 A | 4/1995 | Suda |
| 4,931,047 A | 6/1990 | Broadwin et al. | 5,413,573 A | 5/1995 | Koivukangas |
| 4,931,717 A | 6/1990 | Gray et al. | 5,414,238 A | 5/1995 | Steigerwald et al. |
| 4,938,761 A | 7/1990 | Ensslin | 5,417,719 A | 5/1995 | Hull et al. |
| 4,942,313 A | 7/1990 | Kinzel | 5,422,567 A | 6/1995 | Matsunaga |
| 4,959,606 A | 9/1990 | Forge | 5,423,808 A | 6/1995 | Edwards et al. |
| 4,961,047 A | 10/1990 | Carder | 5,423,809 A | 6/1995 | Klicek |
| 4,961,435 A | 10/1990 | Kitagawa et al. | 5,423,810 A | 6/1995 | Goble et al. |
| 4,966,597 A | 10/1990 | Cosman | 5,425,690 A | 6/1995 | Chang |
| 4,969,885 A | 11/1990 | Farin | 5,425,704 A | 6/1995 | Sakurai et al. |
| 4,992,719 A | 2/1991 | Harvey | 5,430,434 A | 7/1995 | Lederer et al. |
| 4,993,430 A | 2/1991 | Shimoyama et al. | 5,431,672 A | 7/1995 | Cote et al. |
| 4,995,877 A | 2/1991 | Ams et al. | 5,432,459 A | 7/1995 | Thompson |
| 5,015,227 A | 5/1991 | Broadwin et al. | 5,433,739 A | 7/1995 | Sluijter et al. |
| 5,024,668 A | 6/1991 | Peters et al. | 5,436,566 A | 7/1995 | Thompson |
| 5,035,695 A | 7/1991 | Weber, Jr. et al. | 5,438,302 A | 8/1995 | Goble |
| 5,087,257 A | 2/1992 | Farin | 5,443,463 A | 8/1995 | Stern et al. |
| 5,099,840 A | 3/1992 | Goble et al. | 5,445,635 A | 8/1995 | Denen |
| 5,103,804 A | 4/1992 | Abele et al. | 5,451,224 A | 9/1995 | Goble et al. |
| 5,108,389 A | 4/1992 | Cosmescu | 5,458,597 A | 10/1995 | Edwards et al. |
| 5,108,391 A | 4/1992 | Flachenecker | 5,462,521 A | 10/1995 | Brucker et al. |
| 5,122,137 A | 6/1992 | Lennox | 5,472,441 A | 12/1995 | Edwards et al. |
| 5,133,711 A | 7/1992 | Hagen | 5,472,443 A | 12/1995 | Cordis et al. |
| 5,151,102 A | 9/1992 | Kamiyama et al. | 5,480,399 A | 1/1996 | Hebborn |
| 5,152,762 A | 10/1992 | McElhenney | 5,483,952 A | 1/1996 | Aranyi |
| 5,157,603 A | 10/1992 | Scheller et al. | 5,496,312 A | 3/1996 | Klicek |
| 5,160,334 A | 11/1992 | Billings et al. | 5,496,313 A | 3/1996 | Gentelia et al. |
| 5,167,658 A | 12/1992 | Ensslin | 5,500,012 A | 3/1996 | Brucker et al. |
| 5,190,517 A | 3/1993 | Zieve et al. | 5,500,616 A | 3/1996 | Ochi |
| 5,196,008 A | 3/1993 | Kuenecke | 5,514,129 A | 5/1996 | Smith |
| 5,196,009 A | 3/1993 | Kirwan, Jr. | 5,520,684 A | 5/1996 | Imran |
| 5,201,900 A | 4/1993 | Nardella | 5,531,774 A | 7/1996 | Schulman et al. |
| 5,207,691 A | 5/1993 | Nardella | 5,534,018 A | 7/1996 | Wahlstrand et al. |
| 5,230,623 A | 7/1993 | Guthrie et al. | 5,536,267 A | 7/1996 | Edwards et al. |
| 5,233,515 A | 8/1993 | Cosman | 5,540,681 A | 7/1996 | Strul et al. |
| 5,249,121 A | 9/1993 | Baum et al. | 5,540,683 A | 7/1996 | Ichikawa |
| 5,250,063 A | 10/1993 | Abidin et al. | 5,540,684 A | 7/1996 | Hassler, Jr. |
| 5,254,117 A | 10/1993 | Rigby et al. | 5,556,396 A | 9/1996 | Cohen et al. |
| RE34,432 E | 11/1993 | Bertrand | 5,558,671 A | 9/1996 | Yates |
| 5,258,001 A | 11/1993 | Corman | 5,569,242 A | 10/1996 | Lax et al. |
| 5,267,994 A | 12/1993 | Gentelia et al. | 5,571,147 A | 11/1996 | Sluijter et al. |
| 5,267,997 A | 12/1993 | Farin | 5,573,533 A | 11/1996 | Strul |
| 5,281,213 A | 1/1994 | Milder et al. | 5,575,805 A | 11/1996 | Li |
| 5,300,068 A | 4/1994 | Rosar et al. | 5,584,830 A | 12/1996 | Ladd et al. |
| 5,300,070 A | 4/1994 | Gentelia | 5,588,432 A | 12/1996 | Crowley |
| 5,314,445 A | 5/1994 | Degwitz et al. | 5,596,466 A | 1/1997 | Ochi |
| 5,318,563 A | 6/1994 | Malis et al. | 5,599,344 A | 2/1997 | Paterson |
| 5,323,778 A | 6/1994 | Kandarpa et al. | 5,599,345 A | 2/1997 | Edwards et al. |
| 5,324,283 A | 6/1994 | Heckele | 5,599,348 A | 2/1997 | Gentelia et al. |
| 5,326,806 A | 7/1994 | Yokoshima et al. | 5,605,150 A | 2/1997 | Radons et al. |
| 5,330,518 A | 7/1994 | Neilson et al. | 5,613,966 A | 3/1997 | Makower et al. |
| 5,334,183 A | 8/1994 | Wuchinich | 5,620,453 A | 4/1997 | Nallakrishnan |
| 5,334,193 A | 8/1994 | Nardella | 5,624,452 A | 4/1997 | Yates |
| 5,336,220 A | 8/1994 | Ryan et al. | 5,626,575 A | 5/1997 | Crenner |
| 5,341,807 A | 8/1994 | Nardella | 5,628,745 A | 5/1997 | Bek |
| 5,342,356 A | 8/1994 | Ellman | 5,638,003 A | 6/1997 | Hall |
| 5,342,357 A | 8/1994 | Nardella | 5,643,330 A | 7/1997 | Holsheimer et al. |
| 5,342,409 A | 8/1994 | Mullett | 5,647,869 A | 7/1997 | Goble et al. |
| 5,344,424 A | 9/1994 | Roberts et al. | 5,647,871 A | 7/1997 | Levine et al. |
| 5,348,554 A | 9/1994 | Imran et al. | 5,651,780 A | 7/1997 | Jackson et al. |
| 5,370,645 A | 12/1994 | Klicek et al. | 5,658,322 A | 8/1997 | Fleming |
| 5,370,672 A | 12/1994 | Fowler et al. | 5,660,567 A | 8/1997 | Nierlich et al. |
| 5,370,675 A | 12/1994 | Edwards et al. | 5,674,217 A | 10/1997 | Wahlstrom et al. |
| 5,372,596 A | 12/1994 | Klicek et al. | 5,685,840 A | 11/1997 | Schechter et al. |
| 5,376,089 A | 12/1994 | Smith | 5,688,267 A | 11/1997 | Panescu et al. |
| 5,383,874 A | 1/1995 | Jackson | 5,688,270 A | 11/1997 | Yates et al. |
| 5,383,876 A | 1/1995 | Nardella | 5,693,042 A | 12/1997 | Bioarski et al. |
| 5,383,917 A | 1/1995 | Desai et al. | 5,694,304 A | 12/1997 | Telefus et al. |
| 5,385,148 A | 1/1995 | Lesh et al. | 5,695,494 A | 12/1997 | Becker |

| | | | | | | |
|---|---|---|---|---|---|---|
| 5,696,441 | A | 12/1997 | Mak et al. | 6,074,388 | A | 6/2000 | Tockweiler et al. |
| 5,702,386 | A | 12/1997 | Stern et al. | 6,080,149 | A | 6/2000 | Huang et al. |
| 5,702,429 | A | 12/1997 | King | 6,093,186 | A | 7/2000 | Goble |
| 5,707,369 | A | 1/1998 | Vaitekunas et al. | 6,102,497 | A | 8/2000 | Ehr et al. |
| 5,712,772 | A | 1/1998 | Telefus et al. | 6,113,591 | A | 9/2000 | Whayne et al. |
| 5,713,896 | A | 2/1998 | Nardella | 6,113,596 | A | 9/2000 | Hooven |
| 5,718,246 | A | 2/1998 | Vona | 6,123,702 | A | 9/2000 | Swanson et al. |
| 5,720,744 | A | 2/1998 | Eggleston et al. | 6,132,429 | A | 10/2000 | Baker |
| 5,722,421 | A | 3/1998 | Francese et al. | 6,142,992 | A | 11/2000 | Cheng et al. |
| 5,722,975 | A | 3/1998 | Edwards et al. | 6,155,975 | A | 12/2000 | Urich et al. |
| 5,725,536 | A | 3/1998 | Oberlin et al. | 6,162,217 | A | 12/2000 | Kannenberg et al. |
| 5,729,448 | A | 3/1998 | Haynie et al. | 6,171,304 | B1 | 1/2001 | Netherly et al. |
| 5,733,281 | A | 3/1998 | Nardella | 6,188,211 | B1 | 2/2001 | Rincon-Mora et al. |
| 5,749,869 | A | 5/1998 | Lindenmeier et al. | 6,203,541 | B1 | 3/2001 | Keppel |
| 5,749,871 | A | 5/1998 | Hood et al. | 6,210,403 | B1 | 4/2001 | Klicek |
| 5,755,715 | A | 5/1998 | Stern | 6,222,356 | B1 | 4/2001 | Taghizadeh-Kaschani |
| 5,766,165 | A | 6/1998 | Gentelia et al. | 6,228,080 | B1 | 5/2001 | Gines |
| 5,769,847 | A | 6/1998 | Panescu | 6,228,081 | B1 | 5/2001 | Goble |
| 5,772,659 | A | 6/1998 | Becker et al. | 6,231,569 | B1 | 5/2001 | Bek |
| H1745 | H | 8/1998 | Paraschac | 6,235,020 | B1 | 5/2001 | Cheng et al. |
| 5,792,138 | A | 8/1998 | Shipp | 6,238,387 | B1 | 5/2001 | Miller, III |
| 5,797,902 | A | 8/1998 | Netherly | 6,238,388 | B1 | 5/2001 | Ellman |
| 5,797,941 | A | 8/1998 | Schulze et al. | 6,241,725 | B1 | 6/2001 | Cosman |
| 5,814,092 | A | 9/1998 | King | 6,245,065 | B1 | 6/2001 | Panescu |
| 5,817,093 | A | 10/1998 | Williamson, IV et al. | 6,246,912 | B1 | 6/2001 | Sluijter et al. |
| 5,820,568 | A | 10/1998 | Willis | 6,251,106 | B1 | 6/2001 | Becker et al. |
| 5,827,271 | A | 10/1998 | Bussey et al. | 6,258,085 | B1 | 7/2001 | Eggleston |
| 5,827,323 | A | 10/1998 | Klieman et al. | 6,261,285 | B1 | 7/2001 | Novak |
| 5,827,548 | A | 10/1998 | Lavallee et al. | 6,261,286 | B1 | 7/2001 | Goble et al. |
| 5,830,212 | A | 11/1998 | Cartmell | 6,273,886 | B1 | 8/2001 | Edwards |
| 5,836,909 | A | 11/1998 | Cosmescu | 6,275,786 | B1 | 8/2001 | Daners |
| 5,836,943 | A | 11/1998 | Miller, III | 6,293,941 | B1 | 9/2001 | Strul |
| 5,836,990 | A | 11/1998 | Li | 6,293,942 | B1 | 9/2001 | Goble et al. |
| 5,846,236 | A | 12/1998 | Lindenmeier et al. | 6,296,636 | B1 | 10/2001 | Cheng et al. |
| 5,868,737 | A | 2/1999 | Taylor et al. | 6,302,424 | B1 | 10/2001 | Gisinger et al. |
| 5,868,739 | A | 2/1999 | Lindenmeier et al. | 6,306,131 | B1 | 10/2001 | Hareyama et al. |
| 5,868,740 | A | 2/1999 | LeVeen et al. | 6,306,134 | B1 | 10/2001 | Goble et al. |
| 5,871,481 | A | 2/1999 | Kannenberg et al. | 6,309,386 | B1 | 10/2001 | Bek |
| 5,882,567 | A | 3/1999 | Cavallaro et al. | 6,319,451 | B1 | 11/2001 | Brune |
| 5,897,552 | A | 4/1999 | Edwards et al. | 6,325,799 | B1 | 12/2001 | Goble |
| 5,908,432 | A | 6/1999 | Pan | 6,337,998 | B1 | 1/2002 | Behl et al. |
| 5,908,444 | A | 6/1999 | Azure | 6,338,657 | B1 | 1/2002 | Harper et al. |
| 5,913,882 | A | 6/1999 | King | 6,350,262 | B1 | 2/2002 | Ashley |
| 5,921,982 | A | 7/1999 | Lesh et al. | 6,358,245 | B1 | 3/2002 | Edwards |
| 5,925,070 | A | 7/1999 | King et al. | 6,358,268 | B1 | 3/2002 | Hunt et al. |
| 5,931,836 | A | 8/1999 | Hatta et al. | 6,364,877 | B1 | 4/2002 | Goble et al. |
| 5,938,690 | A | 8/1999 | Law et al. | 6,383,183 | B1 | 5/2002 | Sekino et al. |
| 5,948,007 | A | 9/1999 | Starkenbaum et al. | 6,391,024 | B1 | 5/2002 | Sun et al. |
| 5,951,545 | A | 9/1999 | Schilling | 6,391,035 | B1 | 5/2002 | Appleby et al. |
| 5,951,546 | A | 9/1999 | Lorentzen | 6,398,779 | B1 | 6/2002 | Buysse et al. |
| 5,954,686 | A | 9/1999 | Garito et al. | 6,398,781 | B1 | 6/2002 | Goble et al. |
| 5,954,717 | A | 9/1999 | Behl et al. | 6,402,741 | B1 | 6/2002 | Keppel et al. |
| 5,954,719 | A | 9/1999 | Chen et al. | 6,402,743 | B1 | 6/2002 | Orszulak et al. |
| 5,960,544 | A | 10/1999 | Beyers | 6,416,509 | B1 | 7/2002 | Goble et al. |
| 5,961,344 | A | 10/1999 | Rosales et al. | 6,436,096 | B1 | 8/2002 | Hareyama |
| 5,964,758 | A | 10/1999 | Dresden | 6,451,015 | B1 | 9/2002 | Rittman, III et al. |
| 5,971,980 | A | 10/1999 | Sherman | 6,458,121 | B1 | 10/2002 | Rosenstock |
| 5,976,128 | A | 11/1999 | Schilling et al. | 6,458,125 | B1 | 10/2002 | Cosmescu |
| 5,983,141 | A | 11/1999 | Sluijter et al. | 6,464,689 | B1 | 10/2002 | Qin |
| 5,997,565 | A | 12/1999 | Inoue | 6,464,696 | B1 | 10/2002 | Oyama |
| 6,010,499 | A | 1/2000 | Cobb | 6,498,466 | B1 | 12/2002 | Edwards |
| 6,014,581 | A | 1/2000 | Whayne et al. | 6,500,176 | B1 | 12/2002 | Truckai et al. |
| 6,033,399 | A | 3/2000 | Gines | 6,506,189 | B1 | 1/2003 | Rittman, III et al. |
| 6,044,283 | A | 3/2000 | Fein et al. | 6,508,815 | B1 | 1/2003 | Strul |
| 6,053,910 | A | 4/2000 | Fleenor | 6,511,476 | B2 | 1/2003 | Hareyama |
| 6,053,912 | A | 4/2000 | Panescu et al. | 6,511,478 | B1 | 1/2003 | Burnside et al. |
| 6,055,458 | A | 4/2000 | Cochran et al. | 6,514,252 | B2 | 2/2003 | Nezhat et al. |
| 6,056,745 | A | 5/2000 | Panescu et al. | 6,517,538 | B1 | 2/2003 | Jacob et al. |
| 6,056,746 | A | 5/2000 | Goble et al. | 6,524,308 | B1 | 2/2003 | Muller et al. |
| 6,063,075 | A | 5/2000 | Mihori | 6,547,786 | B1 | 4/2003 | Goble |
| 6,063,078 | A | 5/2000 | Wittkampf | 6,558,376 | B2 | 5/2003 | Bishop |
| 6,068,627 | A | 5/2000 | Orszulak et al. | 6,558,385 | B1 | 5/2003 | McClurken et al. |
| 6,074,386 | A | 6/2000 | Goble et al. | 6,560,470 | B1 | 5/2003 | Pologe |

| | | | | | | |
|---|---|---|---|---|---|---|
| 6,562,037 B2 | 5/2003 | Paton | | 7,004,174 B2 | 2/2006 | Eggers et al. |
| 6,565,559 B2 | 5/2003 | Eggleston | | 7,033,356 B2 | 4/2006 | Latterell et al. |
| 6,575,969 B1 | 6/2003 | Rittman, III et al. | | 7,041,096 B2 | 5/2006 | Malis et al. |
| 6,582,427 B1 | 6/2003 | Goble et al. | | 7,041,102 B2 | 5/2006 | Truckai et al. |
| 6,616,658 B2 | 9/2003 | Ineson | | 7,044,948 B2 | 5/2006 | Keppel |
| 6,616,661 B2 | 9/2003 | Wellman et al. | | 7,044,949 B2 | 5/2006 | Orszulak et al. |
| 6,620,157 B1 | 9/2003 | Dabney et al. | | 7,060,063 B2 | 6/2006 | Marion et al. |
| 6,623,423 B2 | 9/2003 | Sakurai | | 7,062,331 B2 | 6/2006 | Zarinetchi et al. |
| 6,629,973 B1 | 10/2003 | Wardell et al. | | 7,063,692 B2 | 6/2006 | Sakurai et al. |
| 6,635,057 B2 | 10/2003 | Harano | | 7,066,933 B2 | 6/2006 | Hagg |
| 6,645,198 B1 | 11/2003 | Bommannan et al. | | 7,070,597 B2 | 7/2006 | Truckai et al. |
| 6,648,883 B2 | 11/2003 | Francischelli | | 7,083,619 B2 | 8/2006 | Truckai et al. |
| 6,652,514 B2 | 11/2003 | Ellman | | 7,087,054 B2 | 8/2006 | Truckai et al. |
| 6,663,623 B1 | 12/2003 | Oyama et al. | | 7,090,689 B2 | 8/2006 | Nagase et al. |
| 6,663,624 B2 | 12/2003 | Edwards | | 7,115,123 B2 | 10/2006 | Knowlton et al. |
| 6,666,860 B1 | 12/2003 | Takahashi | | 7,122,031 B2 | 10/2006 | Edwards et al. |
| 6,676,660 B2 | 1/2004 | Wampler et al. | | 7,131,860 B2 | 11/2006 | Sartor et al. |
| 6,679,875 B2 | 1/2004 | Honda | | 7,137,980 B2 | 11/2006 | Buysse et al. |
| 6,679,882 B1 | 1/2004 | Kornerup | | 7,145,757 B2 | 12/2006 | Shea et al. |
| 6,682,527 B2 | 1/2004 | Strul | | 7,147,638 B2 | 12/2006 | Chapman et al. |
| 6,685,700 B2 | 2/2004 | Behl | | 7,156,842 B2 | 1/2007 | Sartor et al. |
| 6,685,701 B2 | 2/2004 | Orszulak et al. | | 7,160,293 B2 | 1/2007 | Sturm et al. |
| 6,685,703 B2 | 2/2004 | Pearson et al. | | 7,172,591 B2 | 2/2007 | Harano et al. |
| 6,689,131 B2 | 2/2004 | McClurken | | 7,175,618 B2 | 2/2007 | Dabney et al. |
| 6,692,445 B2 | 2/2004 | Roberts et al. | | 7,175,621 B2 | 2/2007 | Heim et al. |
| 6,692,489 B1 | 2/2004 | Heim | | 7,211,081 B2 | 5/2007 | Goble |
| 6,693,782 B1 | 2/2004 | Lash | | 7,214,224 B2 | 5/2007 | Goble |
| 6,712,813 B2 | 3/2004 | Ellman | | 7,220,260 B2 | 5/2007 | Fleming et al. |
| 6,730,080 B2 | 5/2004 | Harano | | 7,241,288 B2 | 7/2007 | Braun |
| 6,733,495 B1 | 5/2004 | Bek | | 7,247,155 B2 | 7/2007 | Hoey et al. |
| 6,733,498 B2 | 5/2004 | Paton | | 7,250,746 B2 | 7/2007 | Oswald et al. |
| 6,736,813 B2 | 5/2004 | Yamauchi et al. | | 7,255,694 B2 | 8/2007 | Keppel |
| 6,740,079 B1 | 5/2004 | Eggers | | 7,276,068 B2 | 10/2007 | Johnson et al. |
| 6,740,085 B2 | 5/2004 | Hareyama | | 7,282,048 B2 | 10/2007 | Goble et al. |
| 6,743,230 B2 | 6/2004 | Lutze et al. | | 7,300,435 B2 | 11/2007 | Wham et al. |
| 6,755,825 B2 | 6/2004 | Shoenman et al. | | 7,303,557 B2 | 12/2007 | Wham et al. |
| 6,757,977 B2 | 7/2004 | Dambal et al. | | 7,314,471 B2 | 1/2008 | Holman |
| 6,758,846 B2 | 7/2004 | Goble et al. | | 7,329,256 B2 | 2/2008 | Johnson et al. |
| 6,773,409 B2 | 8/2004 | Truckai et al. | | 7,329,257 B2 | 2/2008 | Kanehira et al. |
| 6,775,575 B2 | 8/2004 | Bommannan et al. | | D564,662 S | 3/2008 | Moses et al. |
| 6,783,523 B2 | 8/2004 | Qin | | 7,342,754 B2 | 3/2008 | Fitzgerald et al. |
| 6,786,905 B2 | 9/2004 | Swanson et al. | | 7,344,268 B2 | 3/2008 | Jigamian |
| 6,790,206 B2 | 9/2004 | Panescu | | 7,364,577 B2 | 4/2008 | Wham et al. |
| 6,796,981 B2 | 9/2004 | Wham | | 7,367,972 B2 | 5/2008 | Francischelli et al. |
| 6,808,525 B2 | 10/2004 | Latterell et al. | | 7,367,976 B2 | 5/2008 | Lawes et al. |
| 6,824,539 B2 | 11/2004 | Novak | | RE40,388 E | 6/2008 | Gines |
| 6,830,569 B2 | 12/2004 | Thompson | | 7,396,336 B2 | 7/2008 | Orszulak et al. |
| 6,843,789 B2 | 1/2005 | Goble | | 7,491,201 B2 * | 2/2009 | Shields et al. ............. 606/51 |
| 6,849,073 B2 | 2/2005 | Hoey | | 2001/0014804 A1 | 8/2001 | Goble et al. |
| 6,855,141 B2 | 2/2005 | Lovewell | | 2001/0029315 A1 | 10/2001 | Sakurai et al. |
| 6,855,142 B2 | 2/2005 | Harano | | 2001/0031962 A1 | 10/2001 | Eggleston |
| 6,860,881 B2 | 3/2005 | Sturm | | 2002/0035363 A1 | 3/2002 | Edwards et al. |
| 6,864,686 B2 | 3/2005 | Novak | | 2002/0035364 A1 | 3/2002 | Schoenman et al. |
| 6,875,210 B2 | 4/2005 | Refior | | 2002/0052599 A1 | 5/2002 | Goble |
| 6,893,435 B2 | 5/2005 | Goble | | 2002/0068932 A1 | 6/2002 | Edwards |
| 6,923,804 B2 | 8/2005 | Eggers et al. | | 2002/0107517 A1 | 8/2002 | Witt et al. |
| 6,929,641 B2 | 8/2005 | Goble et al. | | 2002/0111624 A1 | 8/2002 | Witt et al. |
| 6,934,134 B2 | 8/2005 | Mori et al. | | 2002/0151889 A1 | 10/2002 | Swanson et al. |
| 6,936,061 B2 | 8/2005 | Sasaki | | 2002/0193787 A1 | 12/2002 | Qin |
| 6,939,346 B2 | 9/2005 | Kannenberg et al. | | 2003/0004510 A1 | 1/2003 | Wham et al. |
| 6,939,347 B2 | 9/2005 | Thompson | | 2003/0060818 A1 | 3/2003 | Kannenberg |
| 6,942,660 B2 | 9/2005 | Pantera et al. | | 2003/0078572 A1 | 4/2003 | Pearson et al. |
| 6,948,503 B2 | 9/2005 | Refior et al. | | 2003/0139741 A1 | 7/2003 | Goble et al. |
| 6,953,461 B2 | 10/2005 | McClurken et al. | | 2003/0153908 A1 | 8/2003 | Goble |
| 6,958,070 B2 | 10/2005 | Witt et al. | | 2003/0163123 A1 | 8/2003 | Goble |
| 6,966,907 B2 | 11/2005 | Goble | | 2003/0163124 A1 | 8/2003 | Goble |
| 6,977,495 B2 | 12/2005 | Donofrio | | 2003/0171745 A1 | 9/2003 | Francischelli |
| 6,979,786 B2 | 12/2005 | Aukland et al. | | 2003/0181898 A1 | 9/2003 | Bowers |
| 6,989,010 B2 | 1/2006 | Francischelli et al. | | 2003/0199863 A1 | 10/2003 | Swanson |
| 6,994,704 B2 | 2/2006 | Qin et al. | | 2003/0225401 A1 | 12/2003 | Eggers et al. |
| 6,994,707 B2 | 2/2006 | Ellman et al. | | 2004/0002745 A1 | 1/2004 | Fleming |
| 6,994,709 B2 | 2/2006 | Iida | | 2004/0015159 A1 | 1/2004 | Slater et al. |
| 7,001,381 B2 | 2/2006 | Harano et al. | | 2004/0015163 A1 | 1/2004 | Buysse et al. |

| | | |
|---|---|---|
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0078035 A1 | 4/2004 | Kanehira et al. |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0236326 A1 | 11/2004 | Schulze et al. |
| 2004/0243120 A1 | 12/2004 | Orszulak et al. |
| 2004/0260279 A1 | 12/2004 | Goble |
| 2004/0260281 A1 | 12/2004 | Baxter, III et al. |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0096645 A1 | 5/2005 | Wellman et al. |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0113826 A1 | 5/2005 | Johnson et al. |
| 2005/0149017 A1 | 7/2005 | Dycus |
| 2005/0149151 A1 | 7/2005 | Orszulak |
| 2005/0182398 A1 | 8/2005 | Paterson |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0025760 A1 | 2/2006 | Podhajsky |
| 2006/0052778 A1 | 3/2006 | Chapman et al. |
| 2006/0074417 A1 | 4/2006 | Cunningham et al. |
| 2006/0079871 A1 | 4/2006 | Plaven et al. |
| 2006/0079888 A1 | 4/2006 | Mulier et al. |
| 2006/0079890 A1 | 4/2006 | Guerra |
| 2006/0116675 A1 | 6/2006 | McClurken et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0038209 A1 | 2/2007 | Buysse et al. |
| 2007/0060919 A1 | 3/2007 | Isaacson et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265612 A1 | 11/2007 | Behnke et al. |
| 2007/0265616 A1 | 11/2007 | Couture et al. |
| 2007/0282320 A1 | 12/2007 | Buysse et al. |
| 2008/0004616 A1 | 1/2008 | Patrick |
| 2008/0009860 A1 | 1/2008 | Odom |
| 2008/0015564 A1 | 1/2008 | Wham et al. |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082094 A1 | 4/2008 | McPherson et al. |
| 2008/0082100 A1 | 4/2008 | Orton et al. |
| 2008/0125767 A1 | 5/2008 | Blaha |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1527747 A2 | 5/2005 |
| EP | 1535581 | 6/2005 |

| | | |
|---|---|---|
| EP | 1535581 A2 | 6/2005 |
| EP | 1 609 430 A1 | 12/2005 |
| EP | 1609430 | 12/2005 |
| EP | 1609430 A1 | 12/2005 |
| EP | 1645235 | 4/2006 |
| EP | 1645240 A2 | 4/2006 |
| EP | 0880220 B1 | 6/2006 |
| EP | 1707143 | 10/2006 |
| EP | 1810628 | 7/2007 |
| EP | 1810630 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2213416 | 8/1989 |
| GB | 2214430 | 9/1989 |
| GB | 2358934 A | 8/2001 |
| JP | 5-5106 | 1/1993 |
| SU | 166452 | 1/1965 |
| SU | 727201 | 4/1980 |
| WO | WO 92/04873 | 4/1992 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO 02/067798 A1 | 9/2002 |
| WO | WO03/090630 | 11/2003 |
| WO | WO 03/090630 A2 | 11/2003 |
| WO | WO 03/090630 A3 | 11/2003 |
| WO | WO03/090635 | 11/2003 |
| WO | WO03/092520 | 11/2003 |
| WO | WO2004/028385 | 4/2004 |
| WO | WO 2004/032776 A1 | 4/2004 |
| WO | WO2004/098385 | 4/2004 |
| WO | WO 2004/073488 A2 | 9/2004 |
| WO | WO2004/103156 | 12/2004 |
| WO | WO 2004/103156 A2 | 12/2004 |
| WO | WO 2005/004734 A1 | 1/2005 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060365 | 7/2005 |
| WO | WO2005/060849 | 7/2005 |

OTHER PUBLICATIONS

International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . ." Journal of Applied Sciences-Yingyong Kexue Xuebao, Shanghai CN, vol. 23 No. 2;(2005-03); 160-164.
International Search Report EP 07008207.8; dated Sep. 5, 2007.
International Search Report EP 07010673.7; dated Sep. 24, 2007.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.

Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 07015601.3; dated Dec. 6, 2007.

* cited by examiner

SYSTEM AND METHOD FOR CONTROLLING RF OUTPUT DURING TISSUE SEALING

BACKGROUND

1. Technical Field

The present disclosure relates to an electrosurgical instrument and method for performing electrosurgical procedures. More particularly, the present disclosure relates to an open or endoscopic bipolar electrosurgical forceps that includes opposing jaw members each having a sealing plate for grasping tissue and supplying electrosurgical energy thereto. The output of electrosurgical energy is adjusted as the sealing plates compress the tissue to prevent cell rupture.

2. Background of Related Art

Electrosurgery involves application of high radio frequency electrical current to a surgical site to cut, ablate, coagulate, cauterize, desiccate or seal tissue. Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, are used for less invasive endoscopic surgical procedures. Electrosurgical forceps (open or endoscopic) utilize mechanical clamping action and electrical energy to effect hemostasis on the clamped tissue. The forceps includes electrosurgical sealing plates which apply the electrosurgical energy to the clamped tissue. By controlling the intensity, frequency and duration of the electrosurgical energy applied through the sealing plates to the tissue, the surgeon can coagulate, cauterize and/or seal tissue.

Tissue sealing procedures involve more than simply cauterizing tissue. In order to affect a proper seal in vessels or tissue, it has been determined that a variety of mechanical and electrical parameters must be accurately controlled: the pressure applied to the tissue; the gap distance between the electrodes (i.e., distance between opposing jaw members when closed about tissue); and amount of energy applied to tissue.

Numerous electrosurgical instruments have been proposed in the past for various open and endoscopic surgical procedures. However, most of these instruments cauterize or coagulate tissue and are not designed to create an effective or a uniform seal. Other instruments generally rely on clamping pressure alone to procure proper sealing thickness and are often not designed to take into account gap tolerances and/or parallelism and flatness requirements which are parameters which, if properly controlled, can assure a consistent and effective tissue seal.

SUMMARY

The present disclosure relates to a vessel or tissue sealing instrument which is designed to manipulate, grasp and seal tissue utilizing jaw members. According to one aspect of the present disclosure an electrosurgical system for sealing tissue is disclosed. An electrosurgical system for sealing tissue is disclosed which includes an electrosurgical forceps having a shaft member and a jaw member disposed at a distal end thereof. The jaw members are movable from a first position in spaced relation relative to one another to at least one subsequent position wherein the jaw members cooperate to grasp tissue therebetween. Each of the jaw members including a sealing plate which communicates electrosurgical energy through tissue held therebetween. The jaw members are adapted to connect to an electrosurgical generator. The system also includes one or more sensors which determine a gap distance between the sealing plates of the jaw members and a microprocessor which is adapted to communicate with the sensor and measure an initial gap distance between the sealing plates as well as to generate a desired gap distance trajectory based on the initial gap distance. The microprocessor is further adapted to communicate with the at least one sensor in real time to adjust output level of the electrosurgical generator as a function of the measured gap distance during the sealing process.

According to a further aspect of the present disclosure a method for sealing tissue is provided. The method includes the steps of providing an electrosurgical forceps for sealing tissue. The forceps includes at least one shaft member having a jaw member disposed at a distal end thereof. The jaw members are movable from a first position in spaced relation relative to one another to at least one subsequent position wherein the jaw members cooperate to grasp tissue therebetween. Each of the jaw members includes a sealing plate adapted to connect to an electrosurgical generator and to communicate electrosurgical energy through tissue held therebetween. One of the jaw members also includes a sensor that determines a gap distance between jaw members. The method also includes the steps of grasping tissue in between the sealing plates and measuring an initial gap distance between the sealing plates and generating a desired gap distance trajectory based on the initial gap distance, wherein the desired gap distance trajectory includes a plurality of target gap distance values. The method further includes the step of adjusting the output of the electrosurgical generator as a function of real time changes in gap distance by the sensor.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical system.

The present disclosure provides for an apparatus, system and method of controlling RF output during sealing. In particular, the RF output applied to tissue grasped between opposing jaw members of a forceps instrument is controlled based on sensed feedback measurements of a gap distance "G" between the opposing jaw members. It has been observed that the relative thickness of various tissues decreases precipitously during the initial stages of a sealing process. In particular, it has been determined that tissue thickness decreases due to cell ruptures caused by constant application of energy and pressure. Since tissue thickness directly corresponds to the gap distance "G" between opposing jaw members, it is envisioned that adjusting RF output based on the desired rate of change of the gap distance "G" controls the decrease in the tissue thickness during the sealing process resulting in a confident, more reliable tissue seal. In other words, controlling the rate at which the thickness of the tissue decreases is beneficial in creating a strong seal since the optimum amount of tissue remains enclosed between the opposing jaw members.

Figure 1A:
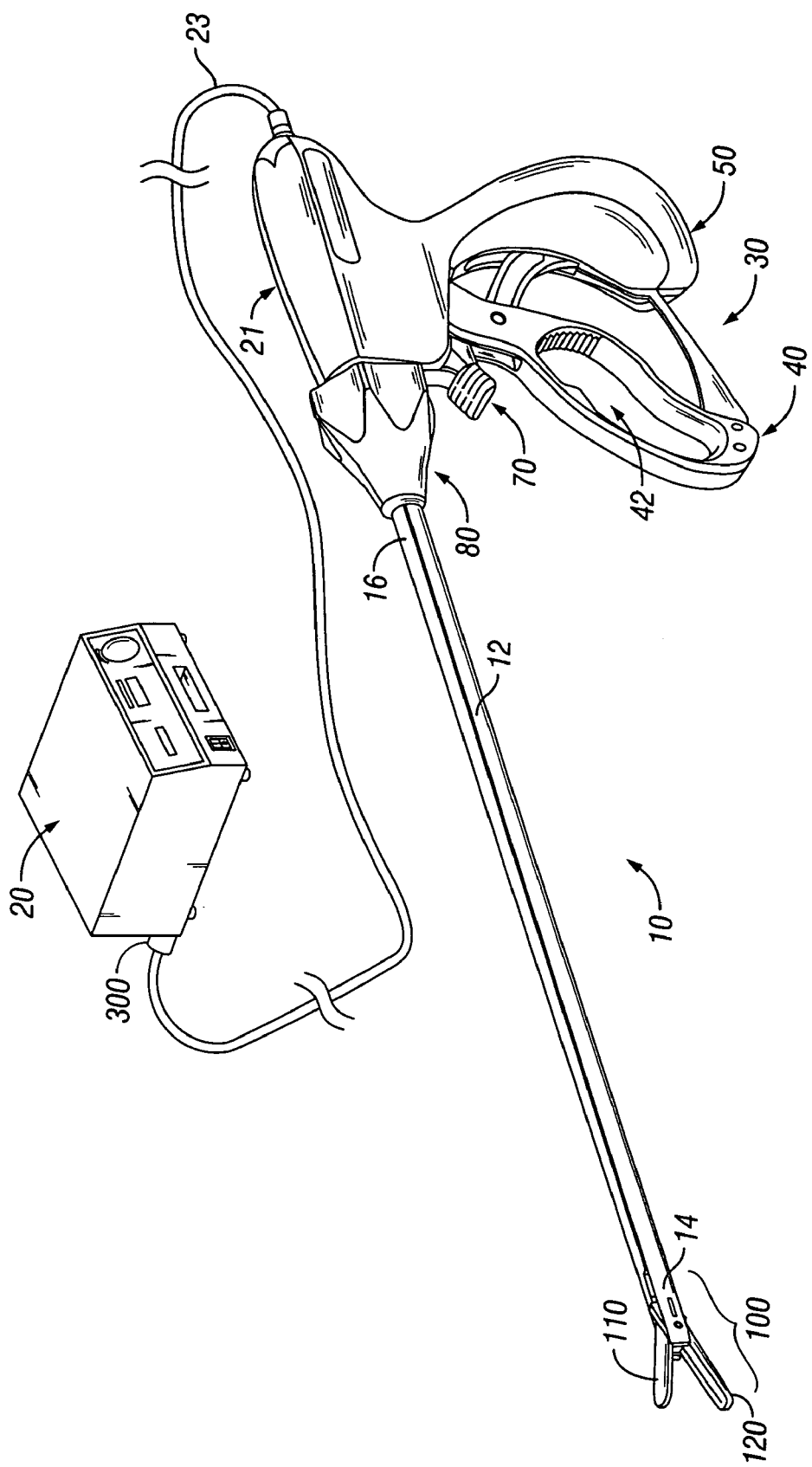
FIG. 1A is a perspective view of an electrosurgical system according to the present disclosure.

With reference to the figures, FIG. 1A shows an electrosurgical system having an endoscopic vessel sealing bipolar forceps 10 electrically coupled to an electrosurgical generator 20 that is adapted to supply electrosurgical high radio frequency (RF) energy thereto. The forceps 10 is shown by way of example and other electrosurgical forceps are also envisioned which allow control of RF output to provide a reliable seal. Those skilled in the art will understand that the invention according to the present disclosure may be adapted for use with either an endoscopic instrument or an open instrument.

It should also be appreciated that different electrical and mechanical connections and other considerations apply to each particular type of instrument. However, the novel aspects with respect to controlling RF output as a function of the gap distance "G" and the operating characteristics of the instruments remain generally consistent with respect to both the open or endoscopic designs.

Figure 1B:
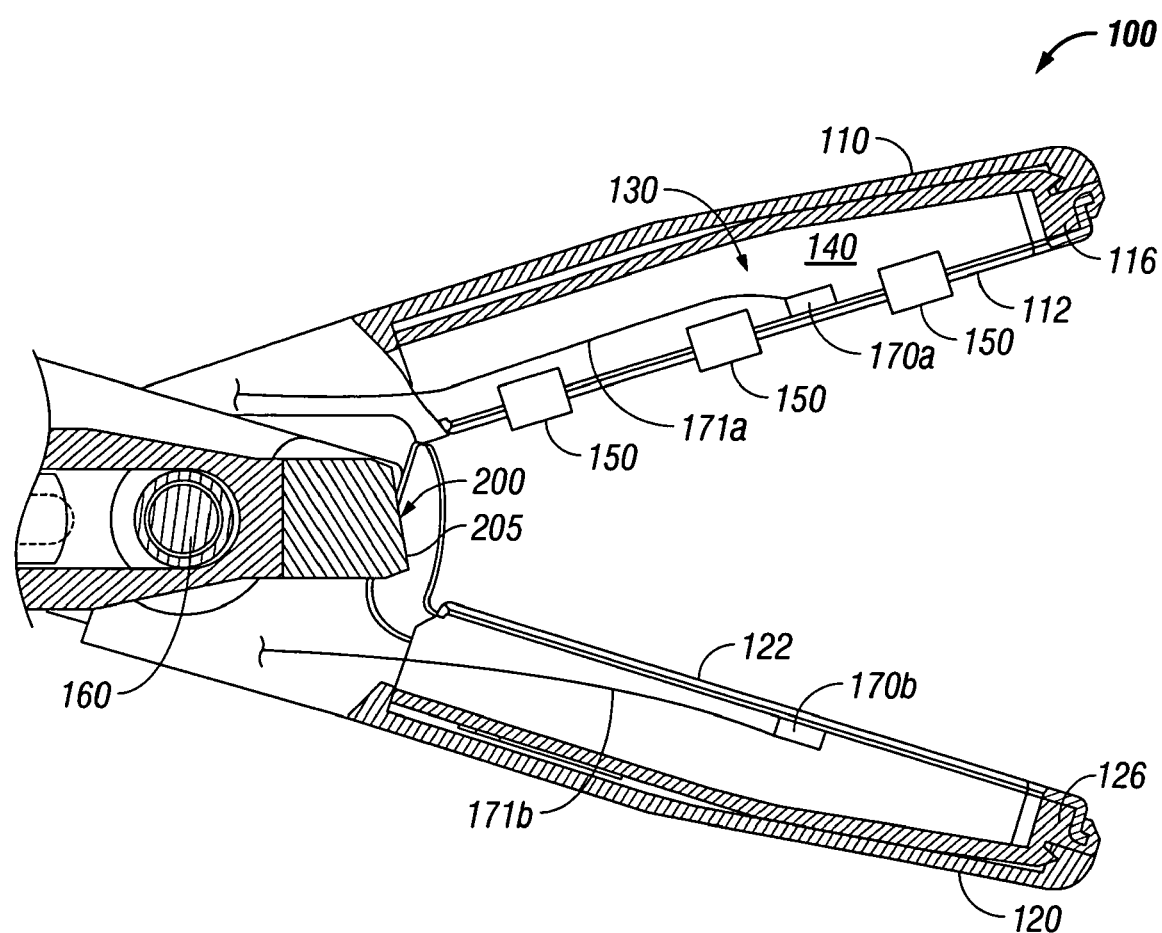
FIG. 1B is a side, partial internal view of an end effector assembly of an endoscopic forceps according to the present disclosure.

FIGS. 1A-1B show the forceps 10 which is configured to support an effector assembly 100 at a distal end thereof. More particularly, forceps 10 generally includes a housing 21, a handle assembly 30, a rotating assembly 80, and a trigger assembly 70 that mutually cooperate with the end effector assembly 100 to grasp, seal and, if required, divide tissue.

The forceps 10 also includes a shaft 12 that has a distal end 14 which mechanically engages the end effector assembly 100 and a proximal end 16 which mechanically engages the housing 21 proximate the rotating assembly 80. In the drawings and in the description which follows, the term "proximal", refers to the end of the forceps 10 which is closer to the user, while the term "distal" refers to the end of the forceps which is further from the user.

Figure 3:
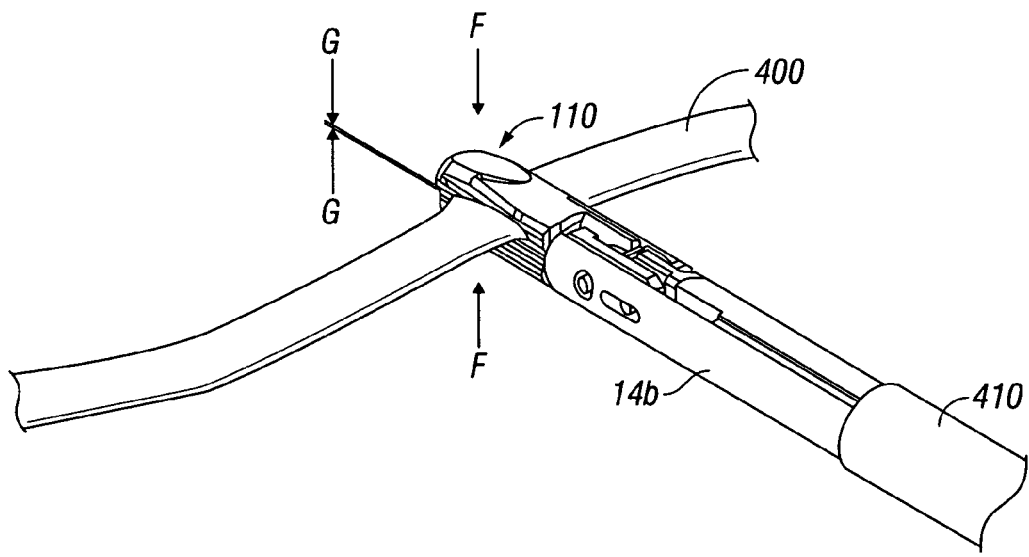
FIG. 3 is a rear, perspective view of the end effector of FIG. 1B shown with tissue grasped therein.

The forceps 10 also includes a plug 300 which connects the forceps 10 to a source of electrosurgical energy, e.g., the electrosurgical generator 20, via an electrical cable 23. Handle assembly 30 includes a fixed handle 50 and a movable handle 40. Handle 40 moves relative to the fixed handle 50 to actuate the end effector assembly 100 and enables a user to grasp and manipulate tissue 400 as shown in FIG. 3.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust the RF energy, waveform, and other parameters to achieve the desired waveform suitable for a particular task (e.g., coagulating, tissue sealing, intensity setting, etc.). It is also envisioned that the forceps 10 may include a plurality of input controls which may be redundant with certain input controls of the generator 20. Placing the input controls at the forceps 10 allows for easier and faster modification of RF energy parameters during the surgical procedure without requiring interaction with the generator 20.

Figure 2:
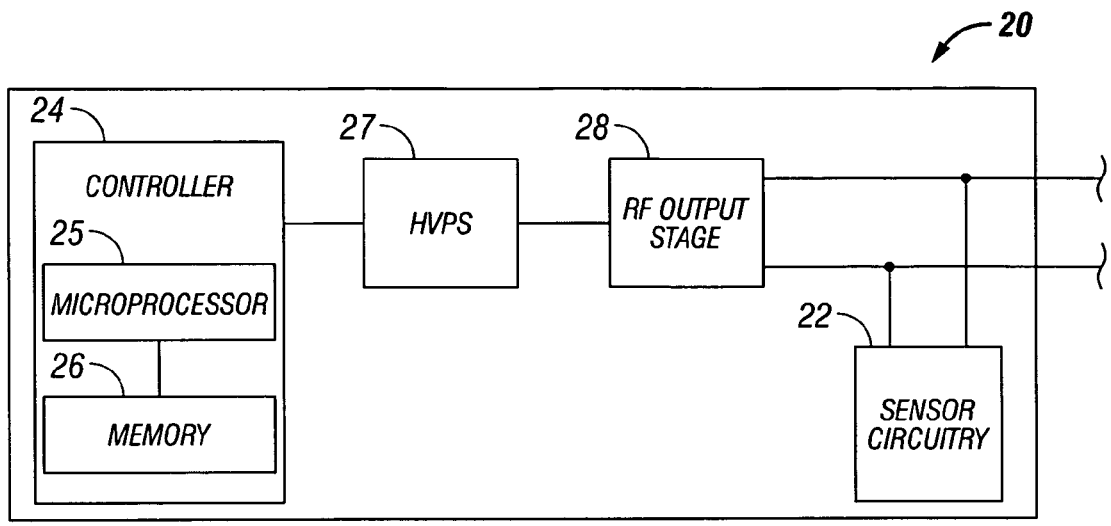
FIG. 2 is a schematic block diagram of a generator system according to the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28 which then converts high voltage DC power into RF energy and delivers the RF energy to the active electrode 24. In particular, the RF output stage 28 generates sinusoidal waveforms of high frequency RF energy. The RF output stage 28 is configured to generate a plurality of waveforms having various duty cycles, peak voltages, crest factors, and other parameters. Certain types of waveforms are suitable for specific electrosurgical modes. For instance, the RF output stage 28 generates a 100% duty cycle sinusoidal waveform in cut mode, which is best suited for dissecting tissue and a 25% duty cycle waveform in coagulation mode, which is best used for cauterizing tissue to stop bleeding.

The controller 24 includes a microprocessor 25 connected to a memory 26 which may be volatile type memory (e.g., RAM) and/or non-volatile type memory (e.g., flash media, disk media, etc.). The microprocessor 25 includes an output port which is connected to the HVPS 27 and/or RF output stage 28 allowing the microprocessor 25 to control the output of the generator 20 according to either open and/or closed control loop schemes.

A closed loop control scheme is a feedback control loop wherein sensor circuitry 22 provides feedback to the controller 24. The sensor circuitry 22 may include a plurality of sensors measuring a variety of tissue and energy properties (e.g., tissue impedance, tissue temperature, output current and/or voltage, gap distance, etc.). Such sensors are within the purview of those skilled in the art. The controller 24 then signals the HVPS 27 and/or RF output stage 28, which then adjust output of DC and/or RF energy, respectively. The controller 24 also receives input signals from the input controls of the generator 20 or the forceps 10. The controller 24 utilizes the input signals to adjust power outputted by the generator 20 and/or performs other control functions thereon.

With references to FIGS. 1A-1B, the end effector assembly 100 includes a pair of opposing jaw members 110 and 120 each having an electrically conductive sealing plate 112 and 122, respectively, attached thereto for conducting electrosurgical energy through tissue 400 held therebetween. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto.

The jaw members 110 and 120 are activated using a drive assembly (not shown) enclosed within the housing 21. The drive assembly cooperates with the movable handle 40 to impart movement of the jaw members 110 and 120 from the open position to the clamping or closed position. Examples of handle assemblies are shown and described in commonly-owned U.S. application Ser. No. 10/389,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

In addition, the handle assembly 30 of this particular disclosure includes a four-bar mechanical linkage, which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

Figure 4:
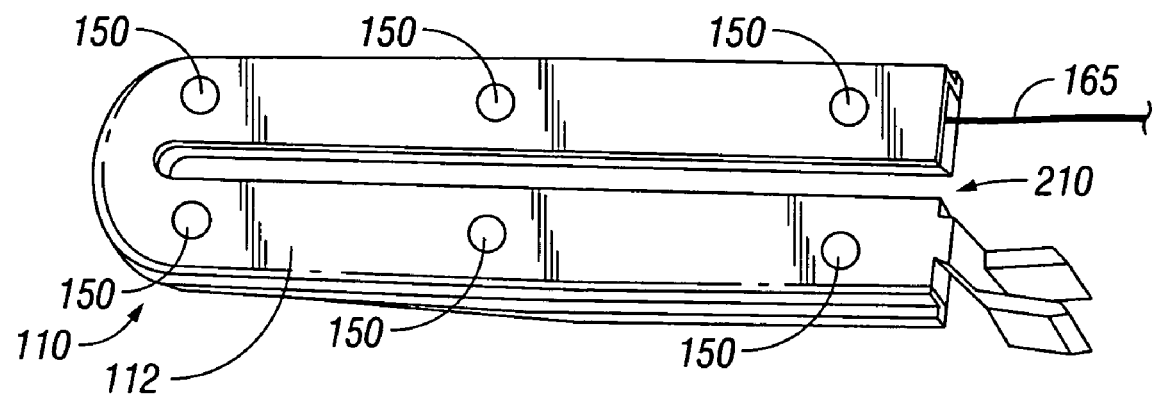
FIG. 4 is an enlarged, perspective view of an electrically conductive sealing plate of the end effector assembly showing a series of selectively adjustable stop members disposed thereon.
Figure 6:
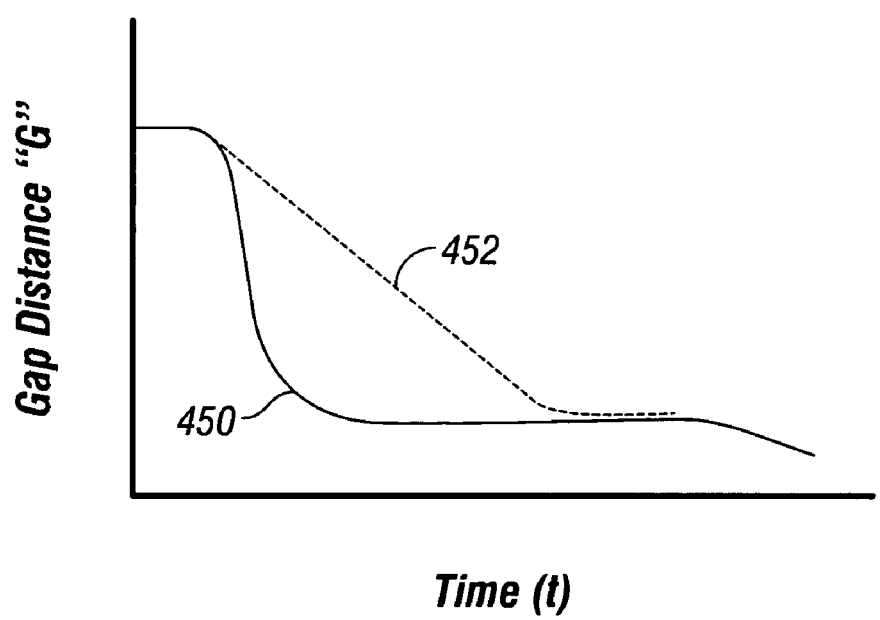
FIG. 6 shows a graph of gap distance "G" versus time (t) utilizing the method of FIG. 5.

As shown in FIGS. 1A-1B, the forceps 10 also includes a trigger 70 which advances a knife 200 disposed within the end effector assembly 100. Once a tissue seal is formed, the user activates the trigger 70 to separate the tissue 400 along the tissue seal. Knife 200 preferably includes a sharpened edge 205 for severing the tissue 400 held between the jaw members 110 and 120 at the tissue sealing site. FIG. 4 shows a longitudinally-oriented channel 210 defined in an electrically conductive sealing plate 112 extending from the proximal end to the distal end thereof. The channel 210 facilitates longitudinal reciprocation of the knife 200 along a preferred cutting plane to effectively and accurately separate the tissue 400 along a formed tissue seal.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1A-1B, the end effector assembly 100 attaches to the distal end 14 of shaft 12. The jaw members 110 and 120 are preferably pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

Since the forceps 10 applies energy through electrodes, each of the jaw members 110 and 120 includes an electrically conductive sealing plate 112 and 122, respectively, disposed on an inner-facing surface thereof. Thus, once the jaw members 110 and 120 are fully compressed about the tissue 400, the forceps 10 is now ready for selective application of electrosurgical energy as shown in FIG. 3. At that point, the electrically conductive plates 112 and 122 cooperate to seal tissue 400 held therebetween upon the application of electrosurgical energy. Jaw members 110 and 120 also include insulators 116 and 126 which together with the outer, non-conductive plates of the jaw members 110 and 120 are configured to limit and/or reduce many of the known undesirable effects related to tissue sealing, e.g., flashover, thermal spread and stray current dissipation as shown in FIG. 1B.

At least one of the jaw members 110 and 120 also includes one or more stop members 150 which limit the movement of the two opposing jaw members 110 and 120 (and sealing plates 112 and 122) relative to one another by acting as a barrier between the two surfaces. It is envisioned that the stop members 150 may be disposed on one or both of the sealing plates 112 and 122 depending upon a particular purpose or to achieve a particular result. Preferably, the stop members 150 extend from at least one of the sealing plates 112, 122 a predetermined distance according to the specific material properties of the stop member 150 (e.g., compressive strength, thermal expansion, etc.).

In order for the stop members 150 to prevent the sealing plates 112, 122 from coming in contact with each other, preferably, the stop members 150 are made from an insulative material, e.g., parylene, nylon and/or ceramic and are dimensioned to limit opposing movement of the sealing plates 112 and 122. Moreover, it is contemplated that any combination of different stop members 150 may be assembled along the sealing plates 112 (and/or 122). A ceramic or insulative coating may be deposited or sprayed onto the tissue engaging plate of the stop member(s) 150. Thermal spraying techniques are contemplated which involve depositing a broad range of heat-resistant and insulative materials on the tissue engaging plates of the stop members 150, high velocity Oxy-fuel deposition, plasma deposition, etc.

FIG. 4 shows one exemplary configuration of the stop members 150 disposed on or protruding from the sealing plate 112. More particularly and as illustrated in FIG. 4, a series of longitudinally-oriented tab-like stop members 150 are disposed along either side of the knife channel 210 of jaw member 110. Preferably, the stop members 150 may be configured in any known geometric or polynomial configuration, e.g., triangular, rectilinear, circular, ovoid, scalloped, etc., depending upon a particular purpose.

The gap distance "G" is used as a sensed feedback to control the thickness of the tissue being grasped. More particularly, a pair of opposing sensors 170c and 170b are configured to provide real-time feedback relating to the gap distance between the sealing plates 112 and 122 of the jaw members 110 and 120 during the sealing process via electrical connection 171a and 171b, respectively. RF energy output is adjusted based on the measured gap distance "G." Consequently, this controls the rate at which tissue grasped between the sealing plates 112 and 122 is being cooked thereby controlling the rate at which the thickness of the tissue being grasped decreases.

The gap distance "G" is directly related to the thickness of tissue being grasped between the sealing plates 112 and 122. Therefore, it is envisioned that the thickness of tissue being grasped may be controlled based on the gap distance "G." As shown in a graph of FIG. 5, thickness of the tissue and therefore the gap distance "G" decrease, as pressure and energy are applied thereto. Tissue thickness decreases for at least two reasons. First, the pressure applied to the tissue by the sealing plates 112 and 122 compresses tissue. Second, RF energy applied to the tissue increases the temperature therein at which point intra-cellular fluids being to boil thereby causing the cells to rupture uncontrollably.

Figure 5:
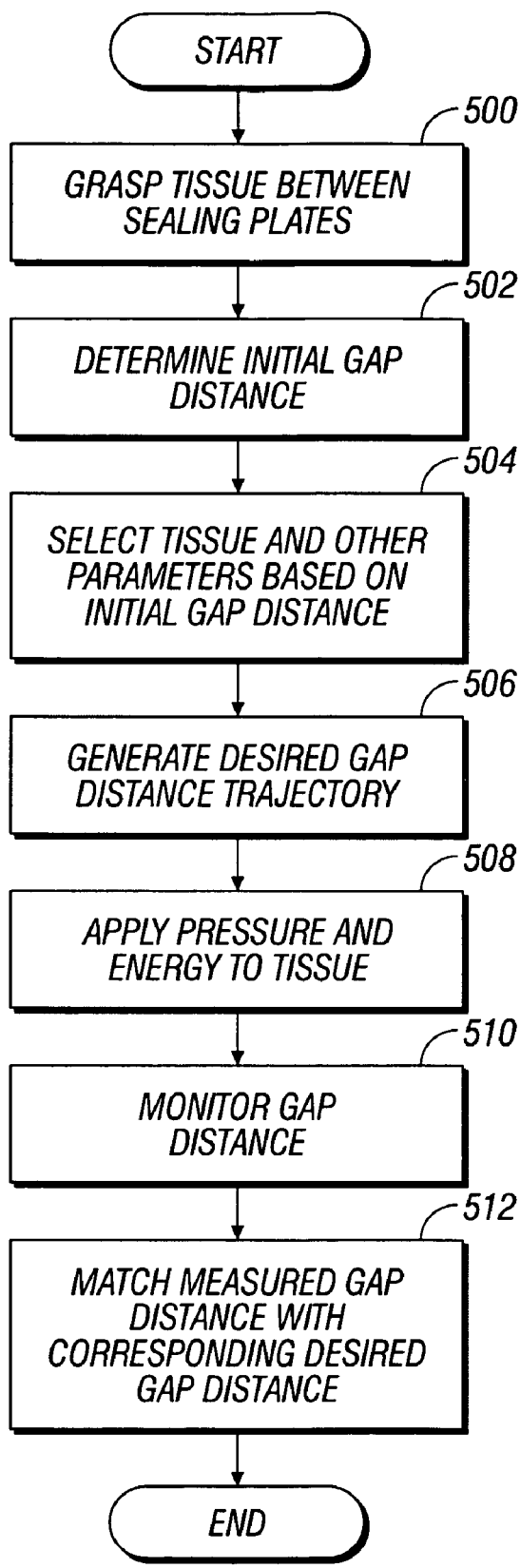
FIG. 5 shows a flow chart showing a sealing method using a bipolar forceps according to the present disclosure.

The graph of FIG. 5 shows a plot 450 of gap distance "G" between electrode plates of a conventional electrosurgical sealing forceps where RF energy is supplied at a constant rate. In the plot 450, the gap distance "G" falls to approximately half of the original value very quickly (e.g., approximately 0.5 seconds). It demonstrates as pressure and energy are applied at a constant rate during initial stages of a sealing procedure, thickness of the tissue rapidly decreases as the tissue is being cooked.

Plot 452 shows a more desirable progression of the gap distance "G." In particular, if the thickness of the tissue decreases at a more controlled rate, grasped tissue remains in the seal area. Conventionally, tissue layers are pressed out of the seal area due to uncontrolled delivery of RF energy, resulting in a less secure seal. Therefore, the controlled decrease of the gap distance "G" of the plot 452 allows for controlled decreases of the tissue thickness. This is accomplished by controlling RF output as a function of the gap distance "G." More specifically, the embodiment of the present disclosure controls delivery of RF energy to tissue during sealing based on the gap distance "G" to maintain the desired rate of cell rupture thereby controlling the thickness of the tissue being grasped.

The sealing method according to the present disclosure is shown in FIG. 5. In step 500, the forceps 10 grasps the tissue 400 using the jaw members 110 and 120. The sealing plates 112 and 122 are activated and are in contact with the tissue 400 but are not fully closed. When the sealing plates 112 and 122 contact the tissue 400 electrosurgical energy is applied thereto and the collagen contained therein is denatured and becomes more mobile (i.e., liquefies).

In step 502, initial gap distance "G" is determined by sensors 170a, 170b which measure the distance between jaw members 110 and 120. The initial gap distance "G" measurement is useful in determining the thickness of the tissue being grasped. The thickness is particularly important since various adjustments to the procedure may be made based on relative tissue thickness. For instance, thin tissue types (e.g., small blood vessels) may require a certain amount of energy and pressure to properly seal desiccation whereas thicker tissue types may require more pressure and more energy. It is envisioned that other tissue parameters may be used to determine thickness and/or properties of the tissue. A second sensor, one of the sensors 170a and 170b, may be adapted to measure boundary conditions, jaw fill, hydration. This may be accomplished by using optical sensors adapted to measure opacity of the tissue. The tissue property measurements are transmitted to the microprocessor 25 wherein adjustments to the generator 20 are made in real-time based on the measurements.

In step 504, energy, tissue and other parameters for constructing a desired trajectory of the gap distance "G" are selected based on the initial gap distance "G." More specifically, the initial gap distance "G" measurement is transmitted to the controller 24 where the tissue thickness is determined as a function thereof. The determination may be accomplished by matching the measured initial gap distance "G" with gap distance "G" values stored in a look-up table stored in memory 26. The look-up table may include a plurality of gap distance "G" values and corresponding tissue thickness values. Upon finding a match, corresponding tissue thickness is obtained. In addition, the look-up table may also include energy and pressure parameters associated with the corresponding tissue thickness. It is envisioned that energy and pressure parameters may be loaded based on the initial gap distance "G" determination without determining the tissue thickness.

In step 506, a desired gap distance "G" trajectory, namely, plot 452 is generated. The gap distance trajectory "G" includes a plurality of desired gap distance "G" values. It is envisioned that the look-up table may include a plurality of parameters such as starting and ending gap distances "G," desired slope(s), etc. The microprocessor 25 uses these parameters to construct the plot 452 (i.e., the desired trajectory) may be linear, quasi-linear, or non-linear.

In step 508, the forceps 10 begins to apply pressure and energy to the tissue 400 using the jaw members 110 and 120 based on the energy and pressure parameters loaded in step 504. The pressure may be constant or be applied to according to a desired pattern (e.g., a control curve).

In step 510, as RF energy is applied to tissue, gap distance "G" is continually monitored and compared with the plot 452 in particular with corresponding desired gap distance "G" values. In step 512, the generator 20 adjusts the energy level based on the measured gap distance "G" by matching measured gap distance "G" with desired gap distance "G." This is accomplished at specific time increments which may be predetermined or dynamically defined. Namely, for every time increment, measured gap distance "G" is compared with a corresponding desired gap distance "G." If the measured gap distance drops off rapidly and is below the desired corresponding gap distance "G" value of the plot 452, the microprocessor 25 adjusts RF output of the generator 20 (e.g., reducing the output).

The apparatus and method according to the present disclosure allow for tissue sealing procedures which retain the collagen at the sealing site which is known to enhance the consistency, effectiveness, and strength of tissue seals. This may be accomplished by using a "slow close" activation to initially denature the collagen and then close the sealing plates under pressure at a predetermined rate. Further details relating to "slow close" activation are disclosed in commonly-owned U.S. application Ser. No. 11/095,123 filed Mar. 31, 2005 entitled "ELECTROSURGICAL FORCEPS WITH SLOW CLOSURE SEALING PLATES AND METHOD OF SEALING TISSUE", the entire content of which being incorporated by reference herein. This allows for limited extrusion of the cured and mixed collagen mass from the sealing site which contributes to an effective and uniform seal.

Figure 7:
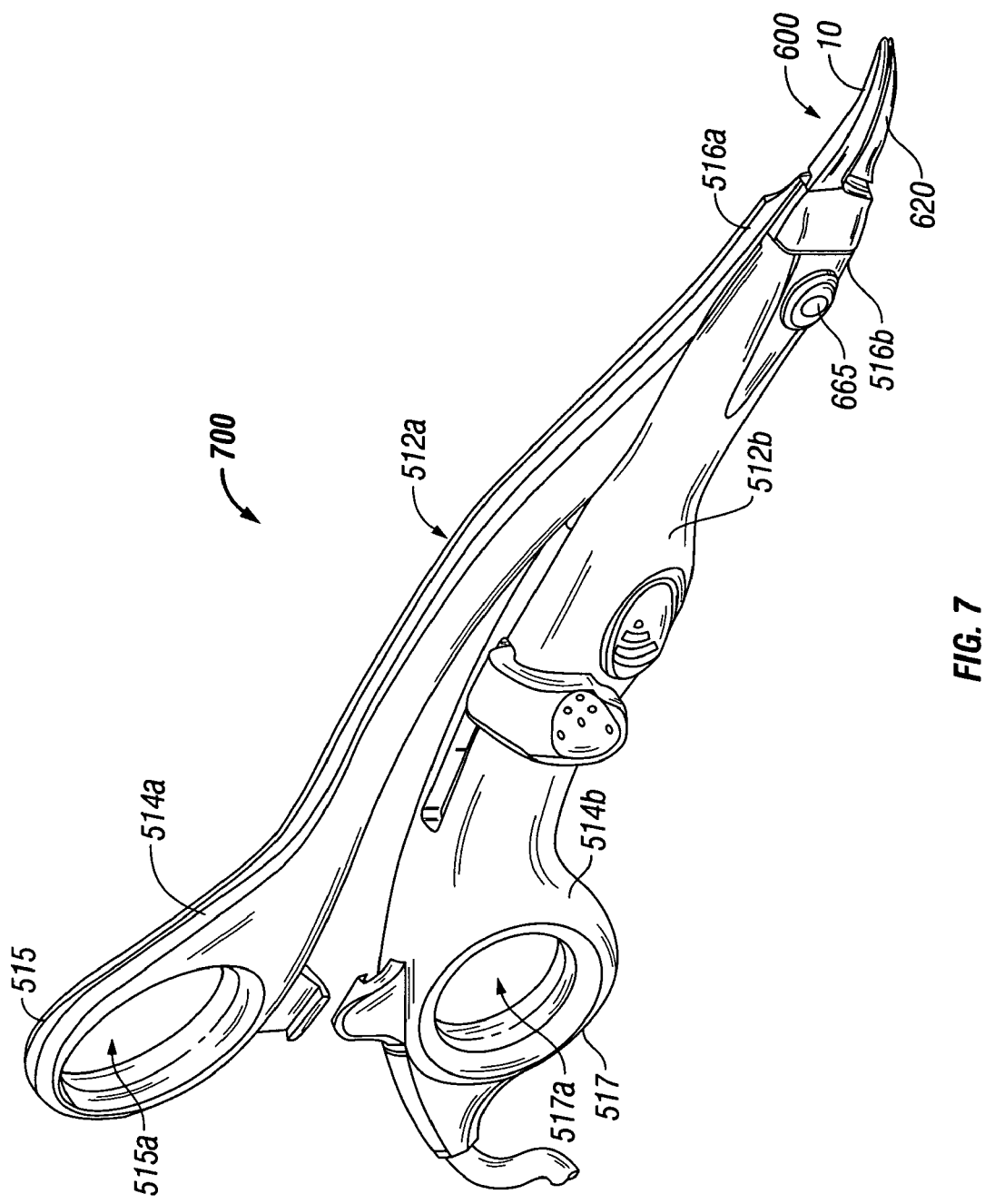
FIG. 7 is a perspective view of an open bipolar forceps which is configured to close at a predetermined rate according to the present disclosure.

From the foregoing and with reference to the various figure drawings, those skilled in the art will appreciate that certain modifications can also be made to the present disclosure without departing from the scope of the same. For example and as mentioned above, it is contemplated that any of the slow closure techniques, methods and mechanisms disclosed herein may be employed on an open forceps such as the open forceps 700 disclosed in FIG. 7. The forceps 700 includes an end effector assembly 600 which attaches to the distal ends 516a and 516b of shafts 512a and 512b, respectively. The end effector assembly 600 includes pair of opposing jaw members 610 and 620 which are pivotally connected about a pivot pin 665 and which are movable relative to one another to grasp vessels and/or tissue. Stop member assembly such as those described with respect to FIGS. 1A-1B, 3, and 4 and sensors 170a and 170b may be disposed within the end effector 600 to regulate the RF energy according to real-time measurements and changes to the gap distance "G" during sealing.

Each shaft 512a and 512b includes a handle 515 and 517, respectively, disposed at the proximal end 514a and 514b thereof each of the handles 515 and 517 define a finger hole 515a and 517a, respectively, therethrough for receiving a finger of the user. Finger holes 515a and 517a facilitate movement of the shafts 512a and 512b relative to one another which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT", the entire content of which being incorporated by reference herein.

In addition, it is also contemplated that the presently disclosed forceps may include an electrical cutting configuration to separate the tissue either prior to, during or after cutting. One such electrical configuration is disclosed in commonly-assigned U.S. patent application Ser. No. 10/932,612 entitled "VESSEL SEALING INSTRUMENT WITH ELECTRICAL CUTTING MECHANISM" the entire contents of which being incorporated by reference herein. Moreover, it is also contemplated that only one sensor in one jaw member may be utilized to measure the initial and real-time changes in the gap distance "G." The sensor may be configured to provide an initial gap distance value to the microprocessor or generator which enables a predetermined starting gap distance value, trajectory and ending gap distance value. The generator then delivers energy according to preset parameters and for pre-set time increments without matching the gap values along a particular curve. In other words, energy is provided based on pre-existing empirical data and not adapted in real-time according to real changes in gap distance "G."

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system for sealing tissue, comprising:
 a forceps including at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and
 each of the jaw members including a sealing plate which communicates electrosurgical energy through tissue held therebetween, the jaw members connected to an electrosurgical generator;
 at least one sensor which determines a gap distance between the sealing plates of the jaw members; and
 a microprocessor programmed to communicate with the at least one sensor to measure an initial gap distance between the sealing plates and to generate a desired gap distance trajectory based on the initial gap distance, the microprocessor programmed to communicate with the at least one sensor in real-time to adjust output level of the electrosurgical generator as a function of the measured gap distance during the sealing process.

2. An electrosurgical system as in claim 1, wherein the desired gap distance trajectory includes a plurality of desired target gap distance values and the microprocessor substantially matches measured gap distance to a corresponding desired target gap distance value and adjusts the generator to deliver the appropriate energy to the tissue.

3. An electrosurgical system as in claim 1, wherein the microprocessor generates the desired gap distance trajectory as a function of at least one of a desired slope, starting gap distance value and desired ending gap distance value.

4. An electrosurgical system as in claim 3, wherein the desired slope, the starting gap distance value and the ending gap distance value are selected as a function of the initial gap distance.

5. An electrosurgical system for sealing tissue as in claim 1, further comprising:
 a knife channel defined along a length of at least one of the sealing plates of one of the jaw members, the knife channel being dimensioned to reciprocate a cutting mechanism therealong; and
 an actuator operatively connected to one of the shaft members which selectively advances the cutting mechanism from a first position wherein the cutting mechanism is disposed proximal to tissue held between the jaw members to at least one subsequent position wherein the cutting mechanism is disposed distal to tissue held between the jaw members.

6. An electrosurgical system as in claim 1 further comprising:
 a second sensor which determines at least one pre-surgical tissue parameter and transmits data pertaining to at least one tissue parameter to the microprocessor.

7. The electrosurgical system as in claim 6, wherein the at least one tissue parameter is selected from a group consisting of boundary conditions, jaw fill and hydration.

8. A method for sealing tissue comprising the steps of:
 providing an electrosurgical forceps for sealing tissue, the forceps including at least one shaft member having an end effector assembly disposed at a distal end thereof, the end effector assembly including jaw members movable from a first position in spaced relation relative to one another to at least one subsequent position wherein the jaw members cooperate to grasp tissue therebetween, each of the jaw members including a sealing plate connected to an electrosurgical generator and communicate electrosurgical energy through tissue held therebetween and at least one of the jaw members including a sensor which determines a gap distance between jaw members;

grasping tissue between the sealing plates and measuring an initial gap distance between the sealing plates;

generating a desired gap distance trajectory based on the initial gap distance, wherein the desired gap distance trajectory includes a plurality of desired target gap distance values; and adjusting the output of the electrosurgical generator as a function of the real-time changes in gap distance by the sensor.

9. A method as in claim 8, wherein the step of generating the desired gap trajectory further includes substantially matching measured gap distance to a corresponding desired target gap distance value.

10. A method as in claim 8, wherein the step of generating the desired gap trajectory further includes generating the desired gap trajectory as a function of at least one of a desired slope, starting gap distance value and desired ending gap distance value.

11. A method as in claim 10, wherein the step of generating the desired gap trajectory further includes selecting the desired slope, the starting gap distance value and the ending gap distance value as a function of the initial gap distance.

12. A method as in claim 8, wherein the step of providing the electrosurgical forceps further includes providing the electrosurgical forceps having:

a knife channel defined along a length of at least one of the sealing plates of one of the jaw members, the knife channel being dimensioned to reciprocate a cutting mechanism therealong; and an actuator operatively connected to one of the shaft members which selectively advances the cutting mechanism from a first position wherein the cutting mechanism is disposed proximal to tissue held between the jaw members to at least one subsequent position wherein the cutting mechanism is disposed distal to tissue held between the jaw members.

13. A method as in claim 8, further comprising the step of:

determining at least one pre-surgical tissue parameter and transmitting data pertaining to at least one tissue parameter to a microprocessor.

14. A method as in claim 13, wherein the step of determining at least one pre-surgical parameter further includes selecting the least one tissue parameter from a group consisting of boundary conditions, jaw fill and hydration.

* * * * *